(12) United States Patent
Wouhaybi et al.

(10) Patent No.: US 10,395,515 B2
(45) Date of Patent: Aug. 27, 2019

(54) SENSOR AGGREGATION AND VIRTUAL SENSORS

(71) Applicant: Intel Corporation, Santa Clara, CA (US)

(72) Inventors: Rita H. Wouhaybi, Portland, OR (US); Denzil Roberts, Portland, OR (US); Vani Desai, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/857,314

(22) Filed: Dec. 28, 2017

(65) Prior Publication Data

US 2019/0043341 A1 Feb. 7, 2019

(51) Int. Cl.
*H04W 4/38* (2018.01)
*G08B 25/14* (2006.01)
(Continued)

(52) U.S. Cl.
CPC .............. *G08B 25/14* (2013.01); *G16H 10/60* (2018.01); *G16H 40/60* (2018.01);
(Continued)

(58) Field of Classification Search
CPC ..... G08B 25/14; G16H 10/60; H04L 63/0428
(Continued)

(56) References Cited

U.S. PATENT DOCUMENTS 7,542,879 B2 * 6/2009 Grichnik ................ G05B 17/02
123/488

9,922,512 B2 * 3/2018 Giri ........................ G05B 15/02
(Continued)

OTHER PUBLICATIONS

Erika McCallister et al., Guide to Protecting the Confidentially of Personally Identifiable Information (PII); Apr. 2010, 59 pages, National Institute of Standards and Technology, Gaithersburg, MD.
(Continued)

*Primary Examiner* — Kerri L McNally
(74) *Attorney, Agent, or Firm* — Schwabe, Williamson & Wyatt, P.C.

(57) ABSTRACT

A sensor aggregator is disclosed that may instantiate virtual sensors providing virtual sensor data. Virtual sensor data may be based at least in part on data shared by transitory sensors that come into an environment associated with the aggregator. An aggregator may have local sensors, e.g., non-transitory sensors associated therewith or disposed therein, or mobile sensors operating in conjunction with or for the aggregator, that may be used to provide sensor data to the aggregator that may also be provided as sensor output from the aggregator. An aggregator may combine different sensor inputs to derive virtual sensors based on received sensor data. In an emergency, an aggregator may assist with exit strategies based conditions sensed in various locations to help route people away from problems. Multiple aggregators may share data and trust mechanisms employed to determine if received sensor data may be trusted/used by an aggregator. And, aggregators may operate to store and forward data, such as to a cloud service, on behalf of a sensor. Accounting/payment systems may be used.

28 Claims, 5 Drawing Sheets

(51) Int. Cl.
*G16H 10/60* (2018.01)
*H04L 29/06* (2006.01)
*H04L 12/28* (2006.01)
*H04W 12/02* (2009.01)
*H04L 29/08* (2006.01)
*G16H 40/60* (2018.01)
*H04L 12/40* (2006.01)

(52) U.S. Cl.
CPC ...... *H04L 12/2803* (2013.01); *H04L 63/0428* (2013.01); *H04L 67/12* (2013.01); *H04W 12/02* (2013.01); *H04L 12/40169* (2013.01); *H04L 2012/4026* (2013.01); *H04W 4/38* (2018.02)

(58) Field of Classification Search
USPC .......................................... 340/506
See application file for complete search history.

(56) References Cited

U.S. PATENT DOCUMENTS

| | | | | |
|---|---|---|---|---|
| 2005/0043934 | A1* | 2/2005 | Hartmann | G05D 1/0825 703/2 |
| 2007/0044539 | A1* | 3/2007 | Sabol | G06Q 10/06 73/19.01 |
| 2008/0224866 | A1* | 9/2008 | Rehman | G08B 13/2417 340/572.1 |
| 2010/0302042 | A1* | 12/2010 | Barnett | G08B 19/00 340/573.1 |
| 2012/0105214 | A1* | 5/2012 | Sanders | H04L 67/12 340/10.42 |
| 2012/0154126 | A1* | 6/2012 | Cohn | H04L 12/2827 340/10.51 |
| 2013/0057394 | A1* | 3/2013 | Andiappan | H04M 1/72569 340/10.51 |
| 2015/0077263 | A1* | 3/2015 | Ali | G05B 23/0216 340/679 |

OTHER PUBLICATIONS

"OFED Overview", retrieved on Apr. 18, 2018; 2 pages, https://openfabrics.org/index.php/openfabric-software.html.

R. Recio et al., "A Remote Direct Memory Access Protocol Specification", Oct. 2007, 57 pages, http://www.ietf.org/rfc/rfc5040.txt.

Brent Curry, "RDMA Consortium Complete Protocol Specifications" Oct. 30, 2002, 2 pages.

"RDMA Consortium: Architectural Specifications for RDMA over TCP/IP", 2009, 1 page, retrieved on Apr. 18, 2018, http://www.rdmaconsortium.org.

* cited by examiner

SENSOR AGGREGATION AND VIRTUAL SENSORS

TECHNICAL FIELD

The present disclosure relates to sensors, and more particularly, to providing virtual sensors and derivative virtual sensors based at least in part on data from one or more sensors.

BACKGROUND AND DESCRIPTION OF RELATED ART

Smart environments, e.g., buildings, cars, parks, etc. are rapidly developing. These environments use sensors to detect various conditions that may be acted upon. When there is a desire to refresh hardware, typically the refresh is a long and complex process that requires a significant investment in worker hours to replace older or defective hardware. While smart environments may be designed to allow access to areas where sensors are installed, it can remain prohibitively expensive or otherwise impractical to update the environment whenever newer and/or better technology becomes available.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

Figure 1:
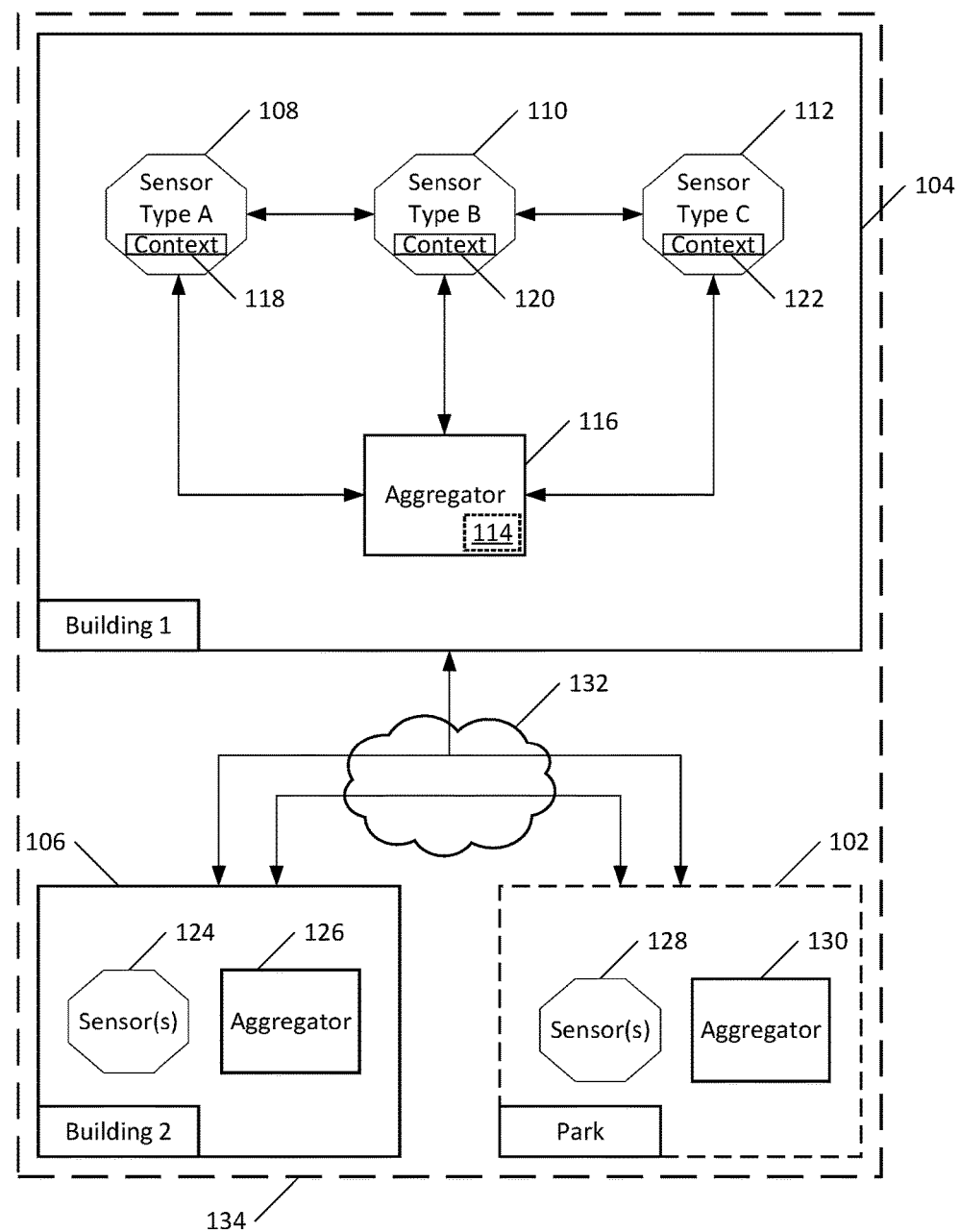
FIG. 1 illustrates an exemplary environment 100.

In the following detailed description, reference is made to the accompanying drawings which form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents. Alternate embodiments of the present disclosure and their equivalents may be devised without parting from the spirit or scope of the present disclosure. It should be noted that like elements disclosed below are indicated by like reference numbers in the drawings.

Various operations may be described as multiple discrete actions or operations in turn, in a manner that is most helpful in understanding the claimed subject matter. However, the order of description should not be construed as to imply that these operations are necessarily order dependent. In particular, these operations do not have to be performed in the order of presentation. Operations described may be performed in a different order than the described embodiment. Various additional operations may be performed and/or described operations may be omitted in additional embodiments. For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). The description may use the phrases "in an embodiment," or "in embodiments," which may each refer to one or more of the same or different embodiments. Furthermore, the terms "comprising," "including," "having," and the like, as used with respect to embodiments of the present disclosure, are considered synonymous.

As used herein, the term "circuitry" or "circuit" may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logic circuit, processor, microprocessor, programmable gate array (PGA), field programmable gate array (FPGA), digital signal processor (DSP) and/or other suitable components that provide the described functionality. Note while this disclosure may refer to a processor in the singular, this is for expository convenience only, and one skilled in the art will appreciate multiple processors, processors with multiple cores, virtual processors, etc., may be employed to perform the disclosed embodiments.

As used herein, the term "computer device" may describe any physical hardware device capable of sequentially and automatically carrying out a sequence of arithmetic or logical operations, equipped to record/store data on a machine readable medium, and transmit and receive data from one or more other devices in a communications network. A computer device may be considered synonymous to, and may hereafter be occasionally referred to, as a computer, computing platform, computing device, etc. The term "computer system" may include any type interconnected electronic devices, computer devices, or components thereof. Additionally, the term "computer system" and/or "system" may refer to various components of a computer that are communicatively coupled with one another. Furthermore, the term "computer system" and/or "system" may refer to multiple computer devices and/or multiple computing systems that are communicatively coupled with one another and configured to share computing and/or networking resources.

Examples of "computer devices", "computer systems", etc. may include cellular phones or smart phones, feature phones, tablet personal computers, wearable computing devices, an autonomous sensors, laptop computers, desktop personal computers, video game consoles, digital media players, handheld messaging devices, personal data assistants, an electronic book readers, augmented reality devices, server computer devices (e.g., stand-alone, rack-mounted, blade, etc.), cloud computing services/systems, network elements, in-vehicle infotainment (IVI), in-car entertainment (ICE) devices, an Instrument Cluster (IC), head-up display (HUD) devices, onboard diagnostic (OBD) devices, dashtop mobile equipment (DME), mobile data terminals (MDTs), Electronic Engine Management System (EEMS), electronic/engine control units (ECUs), electronic/engine control modules (ECMs), embedded systems, microcontrollers, control modules, engine management systems (EMS), networked or "smart" appliances, machine-type communications (MTC) devices, machine-to-machine (M2M), Internet of Things (IoT) devices, and/or any other like electronic devices. Moreover, the term "vehicle-embedded computer device" may refer to any computer device and/or computer system physically mounted on, built in, or otherwise embedded in a vehicle.

As used herein, the term "network element" may be considered synonymous to and/or referred to as a networked computer, networking hardware, network equipment, router, switch, hub, bridge, radio network controller, radio access network device, gateway, server, and/or any other like device. The term "network element" may describe a physical computing device of a wired or wireless communication network and be configured to host a virtual machine. Furthermore, the term "network element" may describe equipment that provides radio baseband functions for data and/or voice connectivity between a network and one or more users. The term "network element" may be considered synonymous to and/or referred to as a "base station." As used herein, the term "base station" may be considered synonymous to and/or referred to as a node B, an enhanced or evolved node B (eNB), next generation nodeB (gNB), base transceiver station (BTS), access point (AP), roadside unit (RSU), etc., and may describe equipment that provides the radio baseband functions for data and/or voice connectivity between a network and one or more users. As used herein, the terms "vehicle-to-vehicle" and "V2V" may refer to any communication involving a vehicle as a source or destination of a message. Additionally, the terms "vehicle-to-vehicle" and "V2V" as used herein may also encompass or be equivalent to vehicle-to-infrastructure (V2I) communications, vehicle-to-network (V2N) communications, vehicle-to-pedestrian (V2P) communications, or V2X communications.

As used herein, the term "channel" may refer to any transmission medium, either tangible or intangible, which is used to communicate data or a data stream. The term "channel" may be synonymous with and/or equivalent to "communications channel," "data channel," "data communications channel," "transmission channel," "data transmission channel," "access channel," "data access channel," "link," "data link," "carrier," "radiofrequency carrier," and/or any other like term denoting a pathway or medium through which data is communicated. Additionally, the term "link" may refer to a connection between two devices through a Radio Access Technology (RAT) for the purpose of transmitting and receiving information.

As used herein, "smart" refers to the application of logic, reasoning, artificial intelligence, deep learning, deep analysis, etc. to an environment, situation, stored data, data stream, etc. The term is intended to expansively and generally refer to any application of machine intelligence (including as influenced by or augmented with human activity and/or input) to a situation or environment in order to determine an action to take (including taking no action). As one example, "smart building" is a term referring to a rapidly expanding market in which nodes may be embedded in a building and/or its rooms and/or amenities during construction and deployment. These nodes could be added to lights, doors, hallways, vending machines, etc. These nodes may contain a set of devices (e.g., sensors, controls, actuators, motors, etc.). Through application of smart technology a building may provide efficiencies of operation not found in conventional buildings. Unfortunately technology improves rapidly and once a building is established with a particular set of internalized components they may rapidly become out of date and/or obsolete. It will be appreciated new sensors, for example, are introduced daily. Consumer products are constantly being developed and release that contain many different sensors. In addition, over time rules and/or regulations may change, or even local codes may change, and smart equipment in a building may no longer be able to function as desired. These issues may then lead to often lengthy time periods for performing upgrades to existing hardware or sensor technology.

FIG. 1 illustrates an exemplary environment 100, which may include, for example, public and private areas, such as a public park 102 or private buildings 104, 106. Illustrated are three sensors 108-112 each respectively having a type A, B and C which are generic types that may represent any kind of sensor. The sensors are communicatively coupled to an aggregator 116. It will be appreciated while the sensors 108-112 are illustrated as separate items, sensors may be incorporated into an aggregator or other device. For example in the illustrated embodiment, item 114 may represent a proximity and motion detector sensor locally connected to the aggregator, e.g. a sensor having a direct communicative coupling by way of a data channel, such as a point-to-point connection (wired or wireless), or as an internal installation within the aggregator, e.g., as a component part.

Sensors 108-112 may be communicatively coupled between themselves over a data channel, such as when incorporated into, for example, a computer device such as a cell phone providing a cellular data network, and/or the sensors may be communicatively coupled with an aggregator over another data channel. In the illustrated embodiment arrows are used to generally present communicative ability and is not intended to limit the number of ways machines, devices, sensors, etc. may be interconnected. In one embodiment, the aggregator 116 may operate as a "data mule", e.g., a device that is present in an environment, such as a smart building 104, that interacts with other devices, such as sensors 108-112 that may be in permanent and/or transitory contact with the environment. For example, while sensor 114 may be installed within the aggregator, the other illustrated sensors 108-112 may be transitory, such as sensor 108 being a sensor in a cell phone carried into the building, or sensor 110 being part of a fitness tracking device (e.g., a health-related Internet of Things wearable device), or sensor 112 being part of vehicle-embedded computer device that may have pulled up to the smart building.

In the illustrated embodiment, sensors 108-114 may measure and carry information about a person (e.g., physiological, phrenological, psychological, etc.), a place (e.g., location, temperature, humidity, air quality, radiation levels, noise levels, traffic, other environmental information, and also indicators for an area's associated data congestion, temporary or permanent environment alterations, such as road closures, regulatory changes, etc.), data related to a thing (e.g., data from a device about the operation or status of the device or data tracked during movement of the device which may include the information described for the other sensors. When a mobile sensor, e.g., sensors 108-112, come in proximity of an aggregator 116, the sensors will contact the aggregator to initiate a transfer of information to the aggregator.

It will be appreciated any data channel and/or communication protocol may be used to exchange information between sensors 108-114 and an aggregator 116. And it will be appreciated protocols may be employed that attempt to minimize systemic costs/burdens in sharing information, attempt to increase throughput, etc. For example, if minimizing power requirements is a goal, then devices containing the sensors may be configured accordingly. Thus, for example, if sensor 108 is in a fully charged cell phone, and sensor 110 is a low power fitness tracker, and both are somewhat distant from the aggregator, it may be a burden to have the fitness tracker seek to communicate directly with the aggregator. Instead, the fitness tracker might engage the phone to act as a proxy and provide its data to the aggregator by way of the phone. It will be appreciated depending on the nature of the data, the phone and fitness tracker might engage in encryption to protect the data. In particular, the fitness tracker might encode its data such that the phone is unable to access it. One such technique, of course, would be to use a public-key cryptosystem based on a public key for the aggregator so that the phone or any other device could be trusted with data to be forwarded to the aggregator. Similarly while the phone may proxy for the fitness tracker, another device, such as an automobile near the building may in turn proxy for the phone since it may be best able to afford to provide data to the aggregator.

The aggregator 116 may spawn one or more virtual sensor to represent the data they are about to obtain. It will be appreciated unlike a traditional device that would have known integrated/known associated sensors, e.g., sensor 114, in the illustrated embodiment the aggregator is instead configured to receive data from multiple sensors that come into its associated environment, e.g. a smart building 104. The aggregator may then instantiate one or more virtual sensor to correspond to the physical sensors 108-112 in its environment. It will be appreciated the virtual sensors need not be a 1:1 correspondence with physical sensors in the environment. In particular, sensors or software operating on top of the physical sensors may be able to provide a feature or function because of a certain combination of physical sensors in the environment. For example a combination of physical sensors providing, for a person, heart rate, breathing rate, skin condensate levels (sweating), degree of agitated movement, eye movement, etc. while individually providing useful data for a person, may also be combined to provide an estimate of stress level, focus, physical well-being, etc. This may also be combined with other data, such as environmental data to help deduce wellbeing of the person, and with other data such as calendar data, to help appreciate context for other data.

It will be appreciated, in one embodiment, environments such as a workplace may have a set of common sensors that regularly enter the environment, and therefore the aggregator may maintain a set of common virtual sensors that provide data that it receives. In this embodiment, there may be a time component associated with the data so that what it reports as sensor data may be considered for staleness. For example, if only once a week a sensor provides the aggregator with measurements of particulate matter in the air in various locations, e.g., as the sensor traveled from some origin to the aggregator, the aggregator will provide particulate sensor information along with an indication of when the data was obtained.

As noted above, encryption may be used to securely transmit, directly or indirectly, data to an aggregator 116. But it will be appreciated a device with one or more sensors may accumulate data that is considered private. For example, health monitors routinely track health statistics a person would consider very private, such as ongoing sugar levels or blood pressure, and never be willing to share that data, while the person is willing to share environmental (air quality) data or share physiological data not considered private or that may be private but willing to share if anonymized (such as heart rate, steps walked, etc.). Therefore sensors (or the associated device using the sensor) may have an associated context 118-122 that may control data sharing. The term "context" is used to refer to any number of personal policies or data restrictions employed by the sensor's owner, rules associated with the environment 104 receiving the data, government rules or regulations (such as data privacy or medical record regulation), or the like. A sensor context includes, but is not limited to, a security context. Sensors, based on the context, may provide copies of their data to the aggregator, and the data, as discussed above, may be anonymized or otherwise grouped with similar data from other sensors. In one embodiment, data may have associated characteristics such as an identifier (e.g., a Globally Unique Identifier (GUID)) associated with the sensor capturing the data, location data, time stamp data, trust or reputation information (or token) associated with the sensor (or of the device or person associated with the data), cost information (e.g., a person may be willing to share data for free to an entity engaging in non-commercial use of the data but charge entities using the data for commercial purposes), etc.

In the illustrated embodiment, the aggregator 116 may verify the identity of the sensor 108-112, its confidence in the data (e.g., based on associated reputation or trust), and any responsibility for data handling, such as an agreement to upload shared and/or private data from the sensor to the cloud on behalf of the sensor. For example, a wearable device incorporated into clothing might be unable to reach the cloud and/or Internet, but it could use encryption to securely provide its private data to the aggregator (or to a proxy that provides it to the aggregator) where the aggregator agrees to forward the data onward. Alternatively, the sensor might include, for example, one or more photograph(s), video(s) or other data the sensor is willing to share, where an aggregator may elect to both keep a copy of the shared information as well as forward it to a cloud storage. It will be appreciated sensors may have an arrangement with an aggregator for forwarding and/or storing data for the sensor, and/or the sensor may have a registration with a registrar or service that is accessible by both sensors and aggregators to allow an aggregator to determine if there is an established arrangement for handling the sensor's data. It will be appreciated a sharing arrangement may include context restrictions on the sharing, or what may be shared publicly, include costs charged by any of the entities involved (e.g., a sensor, aggregator, and cloud service might all have associated costs for sharing data or receiving/processing shared data).

As different sensors 108-112 come contact an aggregator 116, and share their data, an aggregator may in turn present the sensor data to other devices, software, users, etc. as if it were sensed by the aggregator by instantiating virtual sensors corresponding to sensor data shared with the aggregator. Virtual sensor data may be presented along with sensed data from sensors that are associated with the aggregator, e.g., local/fixed sensors such as sensor 114. It will be appreciated trust or confidence information associated with a sensor may be used to either filter out sensed data and not presenting it and/or used to annotate the information so that presented data is given along with an expectation of reliability. For example, if multiple sensors pass through the aggregator environment 104 and many of the sensors are tracking environment data that is consistent with each other, and one device provides environment data inconsistent with the other sensed data, the data from the sensor with inconsistent data may be ignored, or shared with an appropriate flag indicating potential unreliability. Reliability may also be questioned when an aggregator receives one or just a few of a certain type of sensor data. For example, if once device provides radiation readings, it might be reliable, or not, but without other corroborating sources it may be flagged as potentially unreliable. That said, the sensor might, for example, be a device known to be reliable, e.g., certain manufactures may be deemed reliable, or a device might be registered and known to the aggregator (directly or indirectly by way of a registrar), and therefore it may be trusted even if there is only one sensor providing the data.

An aggregator 114 may share its sensed data, e.g., from sensor 114, or virtual sensor data from other transitory sensors, e.g., sensors 108-112, to devices. In one embodiment, the environment, e.g., environment 104, may contain diagnostic devices that may utilize the data from one or more of sensors 108-114. For example, in a medical context where the environment 104 is a hospital, sensor 110 may be part of a fitness tracking device that has been tracking heartrate or other physiological data. This data may be shared in the medical context with diagnostic equipment in the environment. As discussed above, sensor 110 may have an associated context 120 that may ordinarily prevent sharing physiological data, but that will permit it in this environment to assist with medical treatment. In another embodiment, the environment may be a factory, in which technicians may bring in specialized sensors used to evaluate a problem, and the sensed data from these specialized sensors may be obtained by the aggregator and provided to another tool, software, user, etc. to assist with resolving the problem.

In the illustrated embodiment, use of an aggregator in the environment 104 would alleviate the need to continually update or add new sensors as they become available. Instead the aggregator may make use of the sensors within its environment, and receive the benefit of these sensors being regularly updated as technology evolves and newer sensors appear as they are added to consumer or other products. It will be appreciated abstracting sensing operations from data management allows an environment to employ crowd-sourcing of sensing needs, and provide for a limitless number of virtual sensors. Additionally, using aggregator allows for a seamless addition or update to permanent sensors in the environment. As discussed above, sensor 114 may be disposed within the aggregator, or it may simply be associated with it, e.g., by way of some data channel. It will be appreciated newly installed/associated sensors will simply be shared by the aggregator, as it would sensors from transitory sensors.

Additional places where this invention would be useful is in diagnostic situations. For example, imagine a malfunctioning on a factory floor. A team of technicians might show up with specialized and expensive sensing machines to assist in the diagnosis and fixes. These machines will then stream the data which would get associated with the nearest node. Doing so would allow not only to diagnose and correct the problem but also in keeping a record (providence) of the issue and associate it correctly with the context with no manual labeling.

Although the above has focused on one environment 104, it will be appreciated there may be multiple environments 102, 104, 106 communicatively coupled to permit data sharing, which may include sharing information about an environment's "local" sensors 124, 128, as well as associated sensor data. It will be appreciated other environments may also have aggregators 126, 130 That may allow recognizing when a sensor moves between environments, and such recognition may be use at least in part to determining trust for the sensor. Multiple environments may communicate over any kind of data channel, which is generally represented here as cloud 132. It will be appreciated the environments do not have to be physical structures such as a building. An environment may be, for example, be a geographic area, such as a park environment 102. In the illustrated embodiment, the environments may be unrelated entities that separately provide separate aggregators 114, 126, 130 to receive, process and virtualize sensor 108-112, 124, 128 data, that may be shared. One skilled in the art will appreciate that the aggregated sensors from the various environments 102-106 may themselves be combined to form a larger environment 134 incorporating the sub-environments. This larger environment may present an aggregator (or virtual aggregator) providing virtual sensors based on all of the sensors associated with the sub-environments, e.g., sensors 108-112, 124, 128.

Figure 2:
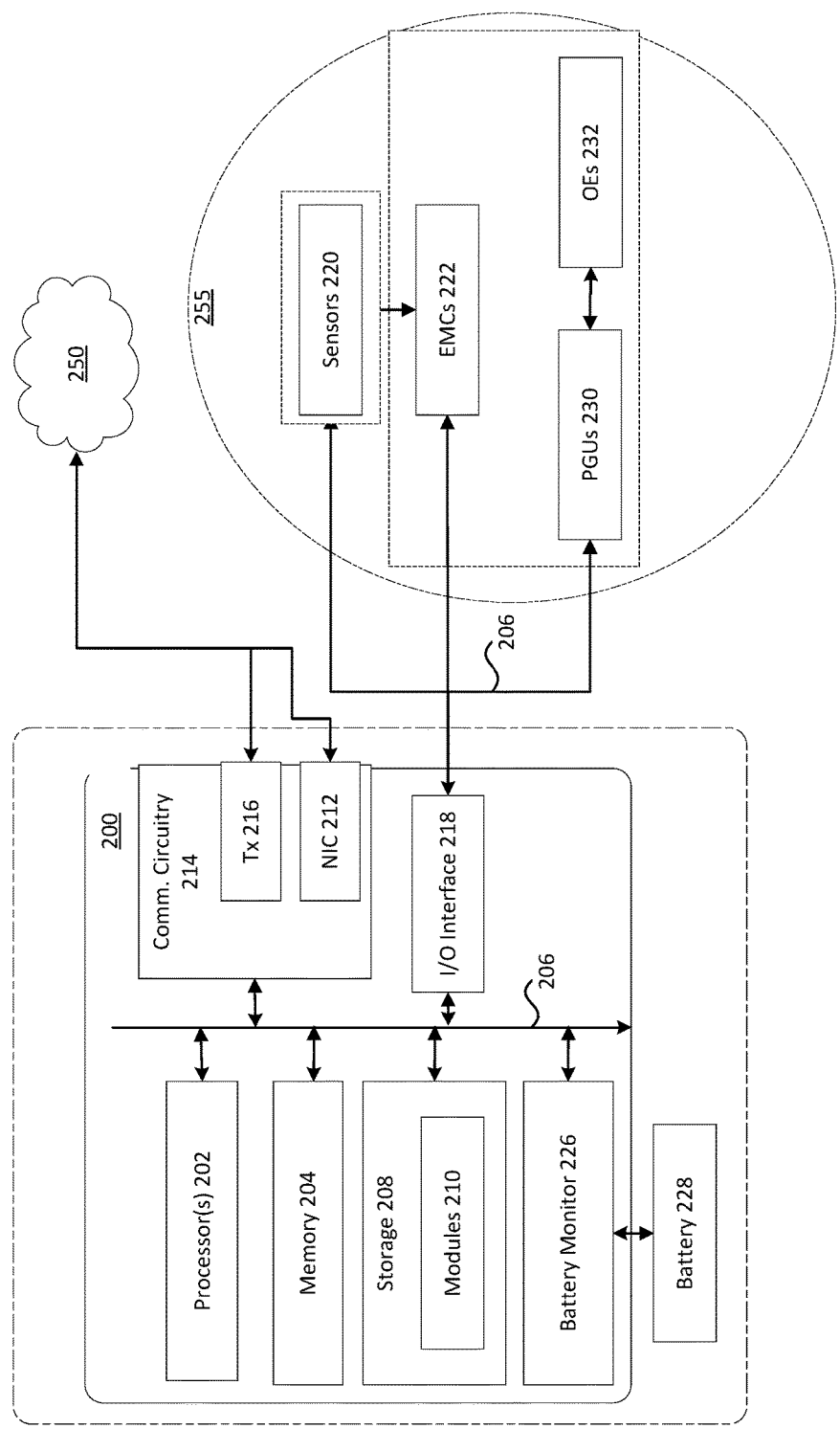
FIG. 2 illustrates an exemplary environment illustrating a computer device 200, in accordance with various embodiments.

FIG. 2 illustrates an exemplary environment illustrating a computer device 200, in accordance with various embodiments. The computer device 200 may include any combinations of the components shown FIG. 2. The components may be implemented as integrated circuits (ICs) or portions thereof, discrete electronic devices, or other modules, logic, hardware, software, firmware, middleware or a combination thereof adapted in the computer device, or as components otherwise incorporated within a chassis of a larger system.

The computer device 200 may be an embedded system or any other type of computer device discussed herein. In one example, the computer device may be employed in or as a device providing sensors and sensor data as discussed herein. In another example, the computer device may be an aggregator in communication with sensors sharing sensed data. The sensors and aggregators may be separate and dedicated and/or special-purpose computer device designed specifically to carry out embodiments discussed herein.

Processor(s) 202 (also referred to as "processor circuitry") may be one or more processing elements configured to perform basic arithmetical, logical, and input/output operations by carrying out instructions. Processor circuitry may be implemented as a standalone system/device/package or as part of an existing system/device/package of, for example, the FIG. 1 sensors 108-114, or aggregator 116. The processor circuitry may be one or more microprocessors, one or more single-core processors, one or more multi-core processors, one or more multithreaded processors, one or more GPUs, one or more ultra-low voltage processors, one or more embedded processors, one or more DSPs, one or more FPDs (hardware accelerators) such as FPGAs, structured ASICs, programmable SoCs (PSoCs), etc., and/or other processor or processing/controlling circuit. The processor circuitry may be a part of a system on a chip (SoC) in which the processor circuitry and other components discussed herein are formed into a single IC or a single package. As examples, the processor circuitry may include one or more Intel Pentium®, Core®, Xeon®, Atom®, or Core M® processor(s); Advanced Micro Devices (AMD) Accelerated Processing Units (APUs), Epyc®, or Ryzen® processors; Apple Inc. A series, S series, W series, etc. processor(s); Qualcomm Snapdragon® processor(s); Samsung Exynos® processor(s); and/or the like.

In embodiments, the processor circuitry 202 may include a sensor hub (not illustrated), which may act as a coprocessor by processing data obtained from the sensors 220. The sensor hub may include circuitry configured to integrate data obtained from each of the sensors by performing arithmetical, logical, and input/output operations. In embodiments, the sensor hub may capable of timestamping obtained sensor data, providing sensor data to the processor circuitry in response to a query for such data, buffering sensor data, continuously streaming sensor data to the processor circuitry including independent streams for each sensor, reporting sensor data based upon predefined thresholds or conditions/triggers, and/or other like data processing functions.

Memory 204 (also referred to as "memory circuitry" or the like) may be circuitry configured to store data or logic for operating the computer device 200. Memory circuitry may include number of memory devices may be used to provide for a given amount of system memory. As examples, the memory circuitry can be any suitable type, number and/or combination of volatile memory devices (e.g., random access memory (RAM), dynamic RAM (DRAM), static RAM (SAM), etc.) and/or non-volatile memory devices (e.g., read-only memory (ROM), erasable programmable read-only memory (EPROM), electrically erasable programmable read-only memory (EEPROM), flash memory, anti-fuses, etc.) that may be configured in any suitable implementation as are known. In one embodiment, memory, such as flash memory or other memory is or may include a memory device that is a block addressable memory device, such as those based on NAND or NOR technologies. A memory device may also include future generation nonvolatile devices, such as a three dimensional crosspoint memory device, or other byte addressable write-in-place nonvolatile memory devices. In one embodiment, the memory device may be or may include memory devices that use chalcogenide glass, multi-threshold level NAND flash memory, NOR flash memory, single or multi-level Phase Change Memory (PCM), a resistive memory, nanowire memory, ferroelectric transistor random access memory (FeTRAM), anti-ferroelectric memory, magnetoresistive random access memory (MRAM) memory that incorporates memristor technology, resistive memory including the metal oxide base, the oxygen vacancy base and the conductive bridge Random Access Memory (CB-RAM), or spin transfer torque (STT)-MRAM, a spintronic magnetic junction memory based device, a magnetic tunneling junction (MTJ) based device, a DW (Domain Wall) and SOT (Spin Orbit Transfer) based device, a thyristor based memory device, or a combination of any of the above, or other memory. The memory device may refer to the die itself and/or to a packaged memory product. In various implementations, individual memory devices may be formed of any number of different package types, such as single die package (SDP), dual die package (DDP) or quad die package (Q17P), dual inline memory modules (DIMMs) such as microDIMMs or Mini-DIMMs, and/or any other like memory devices. To provide for persistent storage of information such as data, applications, operating systems and so forth, the memory circuitry may include one or more mass-storage devices, such as a solid state disk drive (SSDD); flash memory cards, such as SD cards, microSD cards, xD picture cards, and the like, and USB flash drives; on-die memory or registers associated with the processor circuitry 202 (for example, in low power implementations); a micro hard disk drive (HDD); three dimensional cross-point (3D XPOINT) memories from Intel® and Micron®, etc.

Where FPDs are used, the processor circuitry 202 and memory circuitry 204 (and/or device storage circuitry 208) may comprise logic blocks or logic fabric, memory cells, input/output (I/O) blocks, and other interconnected resources that may be programmed to perform various functions of the example embodiments discussed herein. The memory cells may be used to store data in lookup-tables (LUTs) that are used by the processor circuitry to implement various logic functions. The memory cells may include any combination of various levels of memory/storage including, but not limited to, EPROM, EEPROM, flash memory, SRAM, anti-fuses, etc.

Data storage circuitry 208 (also referred to as "storage circuitry" or the like), with shared or respective controllers, may provide for persistent storage of information such as modules 210, operating systems, etc. The storage circuitry may be implemented as solid state drives (SSDs); solid state disk drive (SSDD); serial AT attachment (SATA) storage devices (e.g., SATA SSDs); flash drives; flash memory cards, such as SD cards, microSD cards, xD picture cards, and the like, and USB flash drives; three-dimensional cross-point (3D Xpoint) memory devices; on-die memory or registers associated with the processor circuitry 202; hard disk drives (HDDs); micro HDDs; resistance change memories; phase change memories; holographic memories; or chemical memories; among others. As shown, the storage circuitry is included in the computer device 200; however, in other embodiments, storage circuitry may be implemented as one or more separate devices that are mounted in, for example, an aggregator 116 separate from the other elements of the computer device.

In some embodiments, the storage circuitry 208 may include an operating system (OS) (not shown), which may be a general purpose operating system or an operating system specifically written for and tailored to the computer device 200. The OS may include one or more drivers, libraries, and/or application programming interfaces (APIs), which provide program code and/or software components for modules 210 and/or control system configurations to control and/or obtain/process data from one or more sensors 220 and/or EMCs 222. The modules 210 may be software modules/components used to perform various functions of the computer device and/or to carry out functions of the example embodiments discussed herein. In embodiments where the processor circuitry 202 and memory circuitry 204 includes hardware accelerators (e.g., FPGA cells) as well as processor cores, the hardware accelerators (e.g., the FPGA cells) may be pre-configured (e.g., with appropriate bit streams, logic blocks/fabric, etc.) with the logic to perform some functions of the embodiments herein (in lieu of employment of programming instructions to be executed by the processor core(s)). For example, the modules may comprise logic for the corresponding entities discussed with regard to FIG. 1.

The components of computer device 200 and/or FIG. 1 sensors 108-114, 124, 128 and aggregators 116, 126, 130 may communicate with one another over the bus 206. The bus may include any number of technologies, such as a Local Interconnect Network (LIN); industry standard architecture (ISA); extended ISA (EISA); PCI; PCI extended (PCIx); PCIe; an Inter-Integrated Circuit (I2C) bus; a Parallel Small Computer System Interface (SPI) bus; Common Application Programming Interface (CAPI); point to point interfaces; a power bus; a proprietary bus, for example, Intel® Ultra Path Interface (UPI), Intel® Accelerator Link (IAL), or some other proprietary bus used in a SoC based interface; or any number of other technologies. In some embodiments, bus 206 may be a controller area network (CAN) bus system, a Time-Trigger Protocol (UP) system, or a FlexRay system, which may allow various devices (e.g., sensors 220, EMCs 222, etc.) to communicate with one another using messages or frames. Communications circuitry 214 may include circuitry for communicating with a wireless network or wired network. For example, the communication circuitry may include transceiver (Tx) 216 and network interface controller (NIC) 212, and may include one or more processors (e.g., baseband processors, modems, etc.) dedicated to a particular wireless communication protocol.

NIC 212 may be included to provide a wired communication link to a network 250, e.g., the cloud, and/or other devices. Wired communication may provide an Ethernet connection, an Ethernet-over-USB, and/or the like, or may be based on other types of networks, such as DeviceNet, ControlNet, Data Highway+, PROFIBUS, or PROFINET, among many others. An additional NIC may be included to allow connection with a second network (not shown) or other devices, for example, a first NIC 212 providing communications to the network 250 over Ethernet, and a second NIC providing communications to other devices over another type of network, such as a personal area network (PAN) including a personal computer (PC) device. In some embodiments, the various illustrated components, such as sensors 220, EMCs 222, PGUs 230, etc. may be connected to the system 200 via the NIC 212 as discussed above rather than via the I/O circuitry 218.

The Tx 216 may include one or more radios to wirelessly communicate with the network 250 and/or other devices. The Tx may include hardware devices that enable communication with wired networks and/or other devices using modulated electromagnetic radiation through a solid or non-solid medium. Such hardware devices may include switches, filters, amplifiers, antenna elements, and the like to facilitate the communications over the air (OTA) by generating or otherwise producing radio waves to transmit data to one or more other devices, and converting received signals into usable information, such as digital data, which may be provided to one or more other components of computer device 200. In some embodiments, the various components of the illustrated embodiment, such as sensors 220, EMCs 222, PGUs 230, etc. may be connected to the system 200 via the Tx as discussed above rather than via the I/O circuitry 218. In one example, one or more sensors 220 may be coupled with system 200 via a short range communication protocol, such as BLE or the like. In another example, the PGUs may be coupled with the system via a wireless connection (e.g., via Tx or the like) and operate in conjunction with one or more remote display protocols, such as the wireless gigabit alliance (WiGiG) protocol, the remote desktop protocol (RDP), PC-over-IP (PCoIP) protocol, the high-definition experience (HDX) protocol, and/or other like remote display protocols.

The Tx 216 may include one or multiple radios that are compatible with any number of 3GPP (Third Generation Partnership Project) specifications, notably Long Term Evolution (LTE), Long Term Evolution-Advanced (LTE-A), Long Term Evolution-Advanced Pro (LTE-A Pro), and Fifth Generation (5G) New Radio (NR). It can be noted that radios compatible with any number of other fixed, mobile, or satellite communication technologies and standards may be selected. These may include, for example, any Cellular Wide Area radio communication technology, which may include e.g. a 5G communication systems, a Global System for Mobile Communications (GSM) radio communication technology, a General Packet Radio Service (GPRS) radio communication technology, or an Enhanced Data Rates for GSM Evolution (EDGE) radio communication technology. Other Third Generation Partnership Project (3GPP) radio communication technology that may be used includes UMTS (Universal Mobile Telecommunications System), FOMA (Freedom of Multimedia Access), 3GPP LTE (Long Term Evolution), 3GPP LTE Advanced (Long Term Evolution Advanced), 3GPP LTE Advanced Pro (Long Term Evolution Advanced Pro)), CDMA2000 (Code division multiple access 2000), CDPD (Cellular Digital Packet Data), Mobitex, 3G (Third Generation), CSD (Circuit Switched Data), HSCSD (High-Speed Circuit-Switched Data), UMTS (3G) (Universal Mobile Telecommunications System (Third Generation)), W-CDMA (UMTS) (Wideband Code Division Multiple Access (Universal Mobile Telecommunications System)), HSPA (High Speed Packet Access), HSDPA (High-Speed Downlink Packet Access), HSUPA (High-Speed Uplink Packet Access), HSPA+ (High Speed Packet Access Plus), UMTS-TDD (Universal Mobile Telecommunications System-Time-Division Duplex), TD-CDMA (Time Division-Code Division Multiple Access), TD-SCDMA (Time Division-Synchronous Code Division Multiple Access), 3GPP Rel. 8 (Pre-4G) (3rd Generation Partnership Project Release 8 (Pre-4th Generation)), 3GPP Rel. 9 (3rd Generation Partnership Project Release 9), 3GPP Rel. 10 (3rd Generation Partnership Project Release 10), 3GPP Rel. 11 (3rd Generation Partnership Project Release 11), 3GPP Rel. 12 (3rd Generation Partnership Project Release 12), 3GPP Rel. 13 (3rd Generation Partnership Project Release 13), 3GPP Rel. 14 (3rd Generation Partnership Project Release 14), 3GPP LTE Extra, LTE Licensed-Assisted Access (LAA), UTRA (UMTS Terrestrial Radio Access), E-UTRA (Evolved UMTS Terrestrial Radio Access), LTE Advanced (4G) (Long Term Evolution Advanced (4th Generation)), cdmaOne (2G), CDMA2000 (3G) (Code division multiple access 2000 (Third generation)), EV-DO (Evolution-Data Optimized or Evolution-Data Only), AMPS (1G) (Advanced Mobile Phone System (1st Generation)), TACS/ETACS (Total Access Communication System/Extended Total Access Communication System), D-AMPS (2G) (Digital AMPS (2nd Generation)), PTT (Push-to-talk), MTS (Mobile Telephone System), IMTS (Improved Mobile Telephone System), AMTS (Advanced Mobile Telephone System), OLT (Norwegian for Offentlig Landmobil Telefoni, Public Land Mobile Telephony), MTD (Swedish abbreviation for Mobiltelefonisystem D, or Mobile telephony system D), Autotel/PALM (Public Automated Land Mobile), ARP (Finnish for Autoradiopuhelin, "car radio phone"), NMT (Nordic Mobile Telephony), Hicap (High capacity version of NTT (Nippon Telegraph and Telephone)), CDPD (Cellular Digital Packet Data), Mobitex, DataTAC, iDEN (Integrated Digital Enhanced Network), PDC (Personal Digital Cellular), CSD (Circuit Switched Data), PHS (Personal Handy-phone System), WiDEN (Wideband Integrated Digital Enhanced Network), iBurst, Unlicensed Mobile Access (UMA, also referred to as also referred to as 3GPP Generic Access Network, or GAN standard)), Wireless Gigabit Alliance (WiGig) standard, mmWave standards in general (wireless systems operating at 10-90 GHz and above such as WiGig, IEEE 802.11ad, IEEE 802.11ay, and the like. In addition to the standards listed above, any number of satellite uplink technologies may be used for the uplink transceiver, including, for example, radios compliant with standards issued by the ITU (International Telecommunication Union), or the ETSI (European Telecommunications Standards Institute), among others.

Communication circuitry 214 may implement or support any number of standards, protocols, and/or technologies datacenters typically use, such as networking technology providing high-speed low latency communication. For example, the communication chip(s) may support RoCE (Remote Direct Memory Access (RDMA) over Converged Ethernet), e.g., version 1 or 2, which is a routable protocol having efficient data transfers across a network, and is discussed for example at Internet URL RDMAconsortium-.com. The chip(s) may support Fibre Channel over Ethernet (FCoE), iWARP, or other high-speed communication technology, see for example the OpenFabrics Enterprise Distribution (OFED™) documentation available at Internet URL OpenFabrics.org. It will be appreciated datacenter environments benefit from highly efficient networks, storage connectivity and scalability, e.g., Storage Area Networks (SANS), parallel computing using RDMA, Internet Wide Area Remote Protocol (iWARP), InfiniBand Architecture (IBA), and other such technology. The examples provided herein are thus understood as being applicable to various other communication technologies, both existing and not yet formulated. Implementations, components, and details of the aforementioned protocols may be those known in the art and are omitted herein for the sake of brevity.

The input/output (I/O) interface 218 may include circuitry, such as an external expansion bus (e.g., Universal Serial Bus (USB), FireWire, Thunderbolt, PCI/PCIe/PCIx, etc.), used to connect computer device 200 with external components/devices, such as sensors 220, EMCs 222, PGUs 230, etc. I/O interface circuitry 218 may include any suitable interface controllers and connectors to interconnect one or more of the processor circuitry 202, memory circuitry 204, data storage circuitry 208, communication circuitry 214, and the other components of computer device 200. The interface controllers may include, but are not limited to, memory controllers, storage controllers (e.g., redundant array of independent disk (RAID) controllers, baseboard management controllers (BMCs), input/output controllers, host controllers, etc. The connectors may include, for example, busses (e.g., bus 206), ports, slots, jumpers, interconnect modules, receptacles, modular connectors, etc. The I/O circuitry 218 may couple the system 200 with sensors 220, EMCs 222, PGUs 230, etc. via a wired connection, such as using USB, FireWire, Thunderbolt, RCA, a video graphics array (VGA), a digital visual interface (DVI) and/or mini-DVI, a high-definition multimedia interface (HDMI), an S-Video, and/or the like. Although FIG. 2 shows that the sensors 220, EMCs 222, and PGUs 230 are coupled with the computer device 200 via interface circuitry 218, in other embodiments, the sensors, EMCs 22, and PGUs may be communicatively coupled with the computer device via Tx 216, using short-range radio links, WiFi signaling, or the like.

Sensors 220 may operate as discussed above with respect to FIG. 1 sensors 108-114, 124, 128, and be any device configured to detect events or environmental changes, convert the detected events into electrical signals and/or digital data, and transmit/send the signals/data to the computer device 200 and/or one or more EMCs 222. Some of the sensors 220 may be sensors used for providing computer-generated sensory inputs in an environment which may include computer device 200. Some of the sensors may be sensors used for motion and/or object detection. Examples of such sensors may include, inter alia, charged-coupled devices (CCD), Complementary metal-oxide-semiconductor (CMOS) active pixel sensors (APS), lens-less image capture devices/cameras, thermographic (infrared) cameras, Light Imaging Detection And Ranging (LIDAR) systems, and/or the like. In some implementations, the sensors may include a lens-less image capture mechanism comprising an array of aperture elements, wherein light passing through the array of aperture elements define the pixels of an image. In embodiments, the motion detection sensors may be coupled with or associated with light generating devices, for example, one or more infrared projectors to project a grid of infrared light onto a scene or environment, where an infrared camera may record reflected infrared light to compute depth information.

Some of the sensors 220 may be used for position and/or orientation detection, ambient/environmental condition detection, and the like. Examples of such sensors may include, inter alia, microelectromechanical systems (MEMS) with piezoelectric, piezoresistive and/or capacitive components, which may be used to determine environmental conditions or location information related to the computer device 200. In embodiments, the MEMS may include 3-axis accelerometers, 3-axis gyroscopes, and/or magnetometers. In some embodiments, the sensors may also include one or more gravimeters, altimeters, barometers, proximity sensors (e.g., infrared radiation detector(s) and the like), depth sensors, ambient light sensors, thermal sensors (thermometers), ultrasonic transceivers, and/or the like.

The EMCs 222 may be devices that allow computer device 200 to change a state, position, orientation, move, and/or control a mechanism or system. The EMCs may include one or more switches; haptic output devices, such as actuators and/or motors (e.g., eccentric rotating mass (ERM) actuators, linear resonant actuator (LRA), piezoelectric actuators, servomechanisms, rotary motors, linear motors, and step motors, etc.), thrusters, projectile ejecting devices (e.g., using spring loaded or compressed air/fluid), and/or the like. In embodiments, the EMCs may comprise speakers, a digital rendering module(s) (e.g., a physical object with a digital rendering module therein), and/or another way to control an acoustic energy emission, an electromagnetic radiation emission, an electric energy application, a magnetic field, and an acceleration or deceleration emitted or experienced by a physical object. In embodiments, computer device may be configured to operate one or more EMCs by transmitting/sending instructions or control signals to the EMCs based on detected user interactions or other like events.

Picture generation units (PGUs) 230 may generate light (e.g., based on digital images), which may be directed and/or redirected to optical elements (OEs) 232, e.g., to a display surface. The digital images may be any type of content stored by the storage circuitry 208, streamed from remote devices via the communication circuitry 214, and/or based on outputs from various sensors 220, EMCs 222, and/or other objects, or, as discussed in FIG. 4, generated to assist with an emergency. The OE that combines the generated light with the external light may be referred to as a "combiner element". The PGUs 230 may be one or more electronic devices that create or generate digital images to be directed to OEs 232. The combiner element (as well as other OEs) may be a display surface, which may be fully or partially opaque or transparent, that mixes the digital images output by the projector/PGUs 230 with viewed real-world objects to facilitate augmented reality. In embodiments, the OEs 232 may be a holographic OE, and in some embodiments, the combiner element may be a hologram or holographic image (e.g., transmissive, reflective, etc.).

The battery 228 may power the computer device 200. In embodiments, the battery may be a lithium ion battery, a metal-air battery, such as a zinc-air battery, an aluminum-air battery, a lithium-air battery, a lithium polymer battery, and the like. The battery monitor 226 may be included in the computer device 200 to track/monitor various parameters of the battery, such as a state of charge (SoCh) of the battery, state of health (SoH), and the state of function (SoF) of the battery. The battery monitor may include a battery monitoring IC, which may communicate battery information to the processor circuitry 202 over the bus 206. The bus may allow components of computer device 200 to communicate with one another. The bus may include any number of technologies, such as a Local Interconnect Network (LIN); industry standard architecture (ISA); extended ISA (EISA); Peripheral Component Interconnect Express (PCI); PCI extended (PCIx); PCI express (PCIe); an Inter-Integrated Circuit (I2C) bus; a Parallel Small Computer System Interface (SPI) bus; point to point interfaces; a power bus; a proprietary bus, for example, used in a SoC based interface; or any number of other technologies. Suitable implementations and general functionality of such bus systems are known, and are readily implemented by persons having ordinary skill in the art.

While not shown, various other devices may be present within, or connected to, the computer device 200. For example, I/O devices, such as a display, a touchscreen, or keypad may be connected to the computer device 200 via bus 206 to accept input and display outputs. In another example, the computer device may include or be coupled with positioning circuitry configured to determine coordinates based on signals received from global navigation satellite system (GNSS) constellations, e.g., to derive GPS data. In another example, the communications circuitry 214 may include a Universal Integrated Circuit Card (UICC), embedded UICC (eUICC), and/or other elements/components that may be used to communicate over one or more wireless networks.

Figure 3:
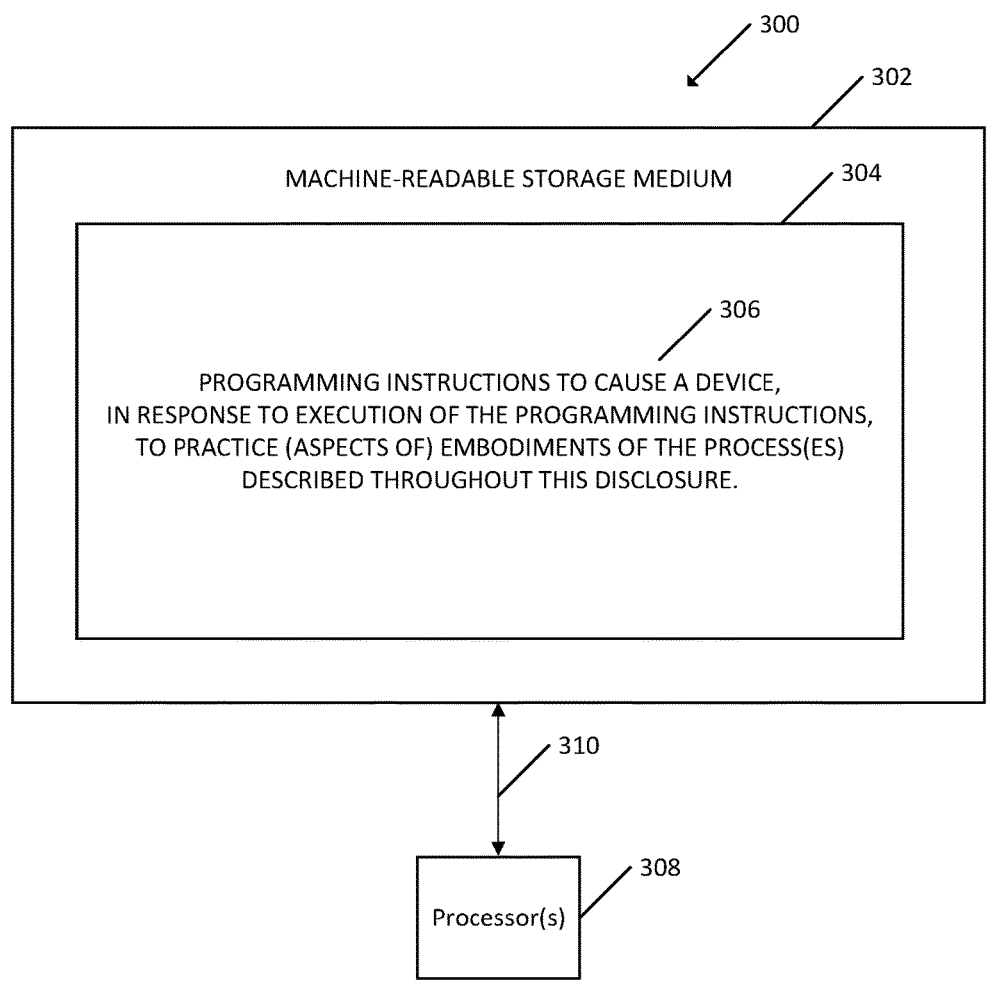
FIG. 3 illustrates an exemplary environment 300 illustrating a storage medium.

FIG. 3 illustrates an exemplary environment 300 illustrating a storage medium that may be transitory, non-transitory or a combination of transitory and non-transitory media, and the medium may be suitable for use to store instructions that cause an apparatus, machine or other device, in response to execution of the instructions, to practice selected aspects of the present disclosure. As will be appreciated by one skilled in the art, the present disclosure may be embodied as methods or computer program products. Accordingly, the present disclosure, in addition to being embodied in hardware as earlier described, may take the form of an entirely software embodiment (including firmware, resident software, micro-code, etc.) or an embodiment combining software and hardware aspects. Furthermore, the present disclosure may take the form of a computer program product embodied in any tangible or non-transitory medium of expression having computer-usable program code embodied in the medium.

In one embodiment, the storage medium is a non-transitory, machine readable (or machine accessible) medium (NTMRM) 302 including associated information 304 that includes at least instructions 306 to direct one or more processor 308 to perform various functions delineated by the embodiments discussed herein. In embodiments, the non-transitory, machine readable medium 302 may be implemented in FIG. 1 sensors 108-114, 124, 128 and/or aggregators 116, 126, 130. The processor may access the non-transitory, machine readable medium 302 over a bus 310. The processor and bus may be the same or similar as described with respect to the processor 202 and bus 206 of FIG. 2. The non-transitory, machine readable medium may include devices described for the mass storage 208 of FIG. 2 or may include optical disks, thumb drives, or any number of other hardware devices or environments providing access to information. In alternate embodiments, machine readable medium may be transitory, e.g., signals.

The NTMRM 302 may include code to direct the processor 308 to obtain data from FIG. 1 sensors 108-114, 124, 128 or FIG. 2 sensors 220. The sensor data may be representative of a physical environment. In one embodiment a modeling engine may direct the processor 308 to generate a model of the physical environment based at least in part on the sensor data. It will be appreciated the model need not be a visual-based model, and may just be various sensor input associated with positional data in any known spatial location system, e.g., longitude/latitude/altitude, 3-point (e.g., XYZ) positions, GPS (Global Positioning System) coordinates, triangulation based on communication towers, association with devices having a known location (e.g., printers, routers and other devices may have a known location that may be imputed to a device passing in range of it), etc. The model may be a suitable collection of data points in the multi-dimensional space connected by various geometric shapes or entities and may include textual and/or contextual information for various surfaces and/or locations within the environment. The model may be generated using any suitable modeling techniques/technologies.

The NTMRM may include code to receive and process user input and/or data associated with an analysis engine to direct the processor to perform some action, such as obtain data from FIG. 1 sensors 108-114, 124, 128 or FIG. 2 sensors 220, interpret user interactions such as gestures and/or speech, interact with other hardware, etc. In some embodiments, sensor and/or other data processed by the processor may include sensor data obtained from wearable technology which may be used to augment or supplement sensor data. In some embodiments, the NTMRM may include code to direct an aggregator to receive and evaluate sensor data and to instantiate virtual sensors and/or derive new virtual sensors based on received sensor data, and to recognize and respond to emergency situations.

The NTMRM may include code of a semantic engine (not illustrated) to direct the processor 302 to determine one or more semantic attributes, which may be used to influence operation of devices executing the code. The semantic engine may determine aspects such as user activity, user attributes, semantic location, social circumstances, ambient or environmental conditions, presence of electronic devices, schedules, communication, etc. that may allow determining what are desirable actions in a given circumstance. User activity semantics may include any information related to user, such as body (or body part) positions or orientations. User attributes may include any information related to user or user preferences.

It will be appreciated any combination of machine readable medium may be utilized, including, for example, but not limited to, an electronic, magnetic, optical, electromagnetic, infrared, or semiconductor system, apparatus, device, or propagation medium. More specific examples (a non-exhaustive list) of the machine readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or machine readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this disclosure, a computer-usable or machine readable medium may be any medium that can contain, store, communicate, propagate, or transport the program for use by or in connection with the instruction execution system, apparatus, or device. The machine readable medium may include a propagated data signal with the computer-usable program code embodied therewith, either in baseband or as part of a carrier wave. The computer usable program code may be transmitted using any appropriate wired or wireless medium.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Cooperative program execution may be for a fee based on a commercial transaction, such as a negotiated rate (offer/accept) arrangement, established and/or customary rates, and may include micropayments between device(s) cooperatively executing the program or storing and/or managing associated data.

Figure 4:
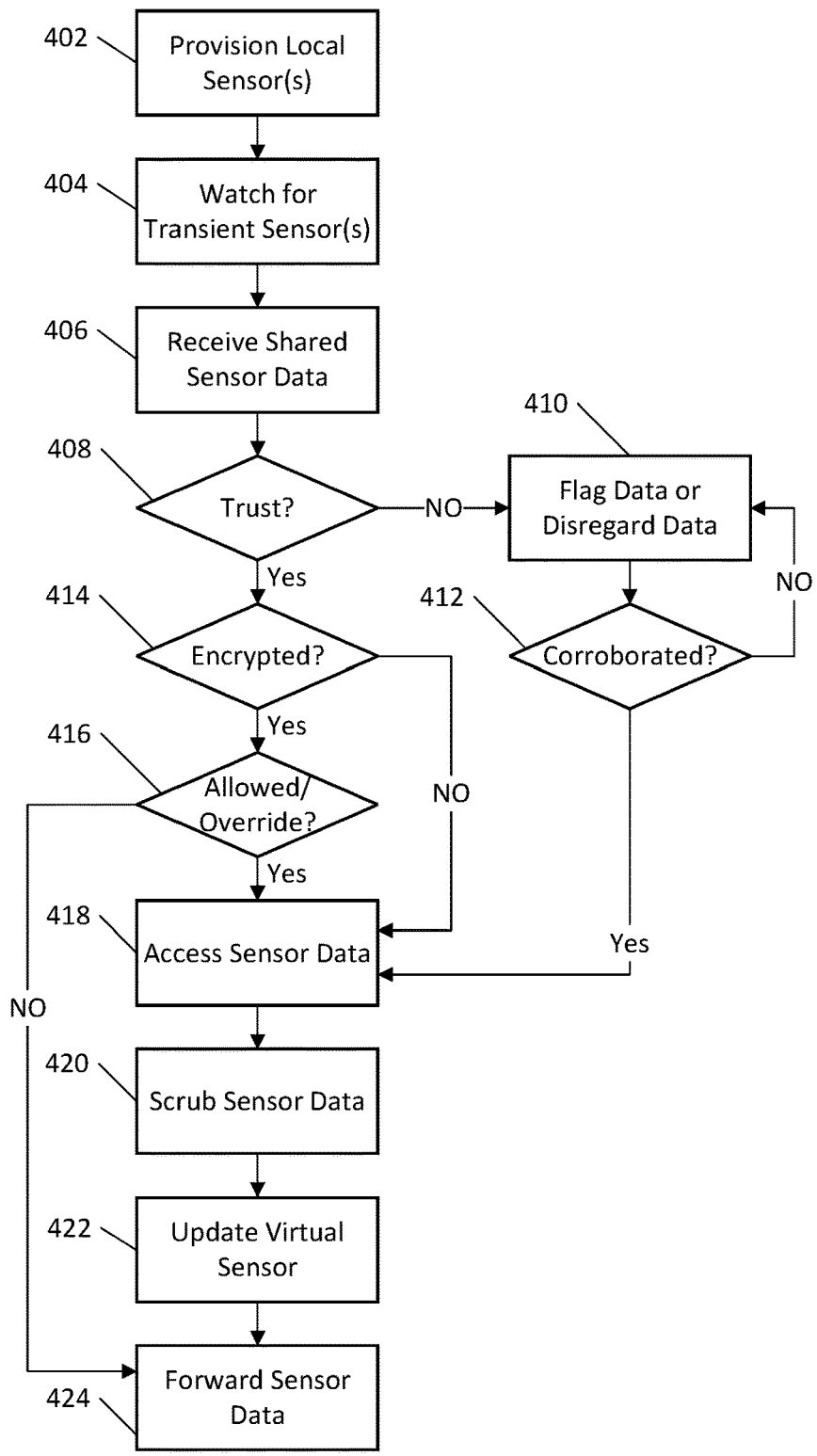
FIG. 4 illustrates an exemplary flowchart 400 in accord with FIG. 1.

FIG. 4 illustrates an exemplary flowchart 400. The illustrated embodiment may concern an exemplary environment in which an aggregator may be installed in the ceiling of a conference room, and the aggregator is providing a sensor service as discussed above allowing local and dynamic sensors to attach to the aggregator to provide their sensor data (in accord with context or other restrictions), and allowing sensors or other devices or systems to request services or data from the aggregator. The illustrated embodiment is in accord with the FIG. 1 embodiment but one skilled in the art will appreciated that the flowchart may be applied to other embodiments discussed herein. It will also be appreciated that while the flowchart illustrates one possible sequence of events, they may occur in a different order and/or in parallel, even though for simplicity a directional chart is presented.

In one embodiment, an aggregator is present that provisions 402, if necessary, any sensors that might be internal to or otherwise permanently associated with the aggregator. It will be appreciated while an aggregator may be expected to opportunistically receive sensor data from sensors or other devices that come within its environment/purview, and thus allow it to take advantage of newer sensors and/or devices as they becomes available and accessible to the aggregator, it may also have non-transitory sensors, e.g. internal/otherwise permanent or semi-permanent associated sensors.

These non-transitory sensors may of course be used as separate data sources, or, in some embodiments, they may be used in combination with transitory sensors to form a derivative virtual sensor aggregating, or fusing, the sensors into a combination that provides greater sensor services than available from any individual sensor in the sensor aggregate, e.g., the sum of the sensors is greater than the parts. The phrase "sensor fusion" refers to combining sensors in various ways to create new sensor, or new virtual sensor, that provides a service and/or sensor data based on the constituent component sensors. An example of sensor fusion may be, for example, outfitting a vehicle with a variety of location, positional, collision, distance, vision, object and/or people detection/recognition, etc. sensors and fusing them together to provide an autonomous guidance system. In a building environment, sensor fusion may be used to receive, for example, heartrate monitors in fitness tracking devices, particulate matter measuring devices (such devices, for example, may track various levels of gasses and/or certain particles in the air), radon/other radiation tracking devices, etc. which when fused may be presented as a virtual air-quality tester capable of not only providing a virtual air quality sensor, but also to apply machine intelligent to determining the effect air quality is having on people in the building. The building may then adjust its operations, e.g., changing heating/cooling, adjusting air recirculation, adding stored air into the building environment, activating air filters, as well as outputting to a display or audio system alerts to people in the building. The building may also output the result of the machine intelligence analysis as another form of data from the virtual air-quality tester.

After provisioning any local sensors, if necessary, an aggregator may then watch 404 for sensors to enter its environment. As discussed above, sensors may share some or all of their data with an aggregator. Sharing may be restricted based on context information associated with the sensor. And the aggregator may provide services to sensors, such as store and forward for the sensor data. It will be appreciated getting data out of sensors and into the cloud can be difficult if the sensor has limited resources, such limited memory. An active sensor may run out of memory before it can offload its tracked data, which would restrict its usefulness. An aggregator may agree to receive the data and be configured to forward the data to the sensor's associated cloud service(s). Sensors may be configured to operate in a first mode, which may be the default/typical operation mode, to conserve its storage and other resources. But if the sensor determines it will be in regular contact with an aggregator, the sensor may operate in a second mode with a higher resolution data capture where at least the extra data is regularly offloaded to the aggregator to free up sensor resources. It will be further appreciated that the sensor context may include cryptographic content, and cloud services login or other information, to enable an aggregator to securely receive information from a sensor, and forward it to the sensor's cloud service for storage. The cryptographic content may be used to enable a sensor to securely share data without exposing it to the aggregator, and similarly the aggregator may securely forward secure data/content onward. It will be understood any number of protocols may be employed by the sensor and aggregator so the sensor may confirm receipt of the data by an aggregator, and if desired its successful forwarding to the cloud.

For example, assuming the conference room example, two people could enter the conference room. A first person could be wearing a smart watch or other wearable device containing a heart rate sensor. The aggregator receives 406 sensor data shared from the first person's device(s)/sensor(s). In the illustrated embodiment, the aggregator may perform a test to determine if 408 the received sensor data may be trusted. It will be appreciated many factors may go into determining trust, such as whether the sensor has been seen before, whether the sensor is providing data that is consistent with data other sensors (or other inputs, network retrieved data, etc.) is providing, whether the sensor is providing an owner identity that can be trusted, whether the manufacturer of the device is known to be reliable, is there an ongoing emergency or event that warrants temporary trust, etc. There are many characteristics of a sensor that may be determined through inspection of the device, its associated context, and the interactions seen with the sensor and between it and other sensors (e.g., has it been successfully used in sensor fusion).

It will be appreciated sensors may randomly enter the aggregator environment and the aggregator may have collected multiple sensor data of the same type, or similar types, and comparing data samples may assist with determining reliability and trust for the data. If previously received data is uncommon and becomes old, the aggregator may apply a staleness factor to the data, giving it minimal reliance and hence limited trust unless the type of information is already known to be relatively static. It will also be appreciated artificial intelligence/machine intelligence may be applied to the analysis of received data to determine a degree of trust. Untrusted data may be discarded or flagged 410 as problematic, but retained. If later data arrives to corroborate 412 it, then the previous data may have simply been an early reporting of data corresponding to, for example, a sudden health or environmental change. Once this is determined, then the retained data may be cleared for use by the aggregator.

It will be appreciated physiological data, such as the heart rate may be considered private data, which, by default, should be encrypted and not be accessible by an aggregator unless the sensor approves of such sharing, e.g., because of a user preference or overriding rule, regulation or condition (e.g., an identified emergency or emergency worker) that causes the sensor to share the information. The aggregator may test to see if 414 shared data is encrypted. If yes, the aggregator may test if 416 access to the data is allowed by the sensor (e.g., the sensor has previously arranged for aggregator access, is encrypting with the aggregator's public key such that the aggregator can decrypt with its private key, or other arrangement for access), or there may be an override. It will be appreciated, for example, a multi-key encryption system may be employed such that overrides may be employed (and tracked if desired for accountability). If access was allowed or otherwise authorized, then the aggregator may access 418 the encrypted data (not shown are operations relating to decrypting the data).

If 414 the data was not encrypted, then the aggregator simply accesses 418 the sensor data. It's been noted that sensors may have associated positioning information, such as GPS data, associated with sensor samples. It will be appreciated even though sensor data sharing might not be thought to be a privacy/security risk to the person sharing the data, when sensor data has associated personally identifiable information (PII), or sensitive personal information (SPI), e.g., data that may be used alone or in combination with other data to identify, contact, or locate the person sharing the sensor data, then while a single sensor reading may or may not be a privacy problem (depending on whether the person would not want the location divulged), a series of sensor readings may be de-facto travel log locating where a person has been, for how long, etc. and sharing that level of detail may be a privacy violation covered by one or more privacy regulations. See, for example, the NIST (National Institute of Standards and Technology) Guide to Protecting the Confidentiality of Personally Identifiable Information (PII) at Internet URL (Uniform Resource Locator) nvlpubs.nist.gov/nistpubs/Legacy/SP/nistspecialpublication800-122.pdf. To alleviate privacy concerns the aggregator may scrub 420 received sensor data to either remove or anonymize PII or equivalent data. It will be appreciated aggregators may be certified to appropriately operate to remove PII.

After scrubbing 420 data, if necessary, the accessed data may then be used to update 422 virtual sensor(s) or other storage and devices associated with the aggregator. In one embodiment, updating a virtual sensor includes instantiating the virtual sensor to report out data accumulated from the first person's sensor data as well as from other sensors providing related information. In this embodiment the virtual sensors correspond to the physical sensors that have entered its environment. However, it will be appreciated other data could be extracted or deduced from a sensor, or from combination with other sensors. For example, there may be sensors for skin temperature, breathing rate, number of steps taken in a time period, activity levels, facial flush detection (from camera sensor data), body language interpretation (from camera sensor data), or body temperature changes, e.g., from a personal thermometer or heat detection/measuring (e.g., infrared) sensor, etc. These sensor values may be combined (e.g., sensor fusion) with, for example, air quality sensors (with associated GPS data) which may detect exposure to certain pollutants, gases, or the like in certain areas. In combination with shared physiological data, an aggregator may instantiate a virtual sensor measuring a likelihood of respiratory distress in the area based on a deduction from air quality measurements and corresponding physiological sensor data from the same locations. These data sources may also be used to instantiate other sensors to represent other discernable conditions such as emotional state, apparent stress, or other physical status and/or risk factor. It will be appreciated an aggregator may provide a virtual respiratory distress sensor with publicly accessible data, while also treating the underlying data as private to be encrypted/protected/anonymized/discarded as needed.

It will be appreciated different sensor data may present an aggregator with a survey of the surrounding areas to facilitate identifying an area or areas under distress. Although one might think data corresponding to areas outside the aggregator's environment are irrelevant, it may be necessary to adjust, for example, air quality and/or temperature to respond to the external influence, or to inform neighboring buildings or other environments of unusual sensor data. After updating 422 a virtual sensor, deriving sensors, etc. the aggregator may, as discussed above, forward 424 received sensor data to a cloud service. It will be appreciated the aggregator may store and/or forward any data of the wearable associated with the first person. Thus for example a tablet could share sensor data along with photos with the aggregator, and while the aggregator may ignore the photos, it may forward the photos to a cloud photo storage program on behalf of the sensor. It will be further appreciated that while the aggregator may scrub 420 sensor data for its use, the aggregator may forward received sensor data on behalf of the sensor with PII or other information since the data is being forwarded on behalf of and at the request of the device(s)/sensor(s) in use by the person agreeing to the forwarding.

As noted above, if we assume the illustrated embodiment is performed in a conference room, a second person could enter the room, and the aggregator would be watching 404 for entry of the second person's sensors into its environment. On detecting sensors, the aggregator may receive 406 sensor data from the second person's device(s). If the sensor data being shared is directly relevant to the operation of the building, e.g. it may contain air quality data, travel data, air temperature data, etc., this data has direct applicability to operation of the building, and it may be received and applied to operation of the building. However, as discussed above, the received sensor data is assumed to be cross-referenced with location data such as GPS coordinates. And while the data regarding air quality might not be considered private, the related location data may be PII, particularly when viewed across multiple sensor samples. The aggregator may determine whether to keep the PII (based on circumstance or arrangement with the sensor/user of the sensor), or the sensor may flag the PII as data the aggregator must anonymize on receipt to minimize privacy risk to the sharing party.

It will be appreciated privacy may be addressed, at least in part, by a sensor and/or aggregator applying filters when accessing 418 sensor data to minimize unwanted PII sharing. For example, in the air quality example, a geofence may be applied and location data is either not shared or is filtered out by the aggregator if is more than a desired distance from the aggregator (e.g., a fixed distance, or dynamically determined based on other factors), or not from a desired location (e.g. in a building or it's parking lot). In one embodiment, if multiple sensors (transitory or fixed) exist in a certain area, there may be system policies that, along with sensor context, could be shared and inherited based on location, role, time spent in a building, and policies of other buildings and spaces the sensor(s)/person(s) visit. Policies could be used to define geofence and/or other characteristics that may be used to determine what data is shared, what data aggregators keep, or receive and modify (e.g., anonymize) before use.

In one embodiment, an aggregator may implement trust 408 through use, at least in part, of local policies that may differ from other aggregators. Aggregators in different locations may have differing levels of concern for the data they receive. Or they may employ differing levels of trust required before accessing 418 the sensor data. In one embodiment, an aggregator may employ sensor tokens (which may be provided, e.g., to the device with the sensor after authentication/registration with the aggregator/system providing the aggregator) which the sensor may provide when offering data and/or request the data forward 424 service. These tokens may be tied into a trust level. For example, a sensor could be given a token allowing limited data sharing and limited or simply deny the forwarding service. The token's access rights may be shared across an organization, geographical location, or even across multiple sites which may be separate entities but operating within a common framework.

In one embodiment, as a sensor becomes known to one aggregator, such as from an employee regularly passing through the aggregator's environment, it may update the trust level for a sensor and propagate it across the relevant system(s) to which the token relates. Trust levels may change, for example, based on the amount data offered by a sensor, the amount of data transfer requested, and the quality of the data. It will be appreciated that fixed sensors local to the aggregator, sensors given to an employee by an employer providing the aggregator, or sensors on equipment/carts/luggage/etc. that regularly move throughout an area, e.g., in a building with multiple aggregators, these sensors may have a fixed trust level to ensure these "trusted" sensors are trusted by aggregators and allowed to make use of its services.

Regarding trust 408 and corroboration 412 it will be appreciated baseline reliable data may be maintained by deploying sensors along with the aggregator where they may be used to calibrate received 406 sensed data. For example, an air quality sensor managed by an IT department could be mounted on a coffee cart which typically travels frequently throughout an office building, and which may come in contact with aggregators throughout the building. The sensor(s) on this cart, since issued by the IT departments, may be trusted at a high trust level. When other sensors, such as those provided by individuals with a lower associated trust token measure air quality, their reported data is compared for the same time range and/or location to those reported sensors with a higher trust level. Lower level sensors lacking a history with an aggregator or the system suing the aggregator(s) may as discussed above flag 410 the data a being potentially unreliable. An aggregator may apply rules/heuristics/machine intelligence/etc. to sensor contact to determine raising a sensor's trust level. For example, after a period of regular contact, or after a number of sensor reports corroborated by IT sponsored sensors, etc., the sensor's trust level may be upgraded and data from that sensor may be trusted and used by the aggregator. Also as discussed above, upgraded trust levels may be shared within the aggregator's system as well as with other entities. It will be appreciated if transient sensors are often contrasting local/fixed/provided sensors, this may suggest that the local/fixed/provided sensors need to be reviewed/updated. Also, if the type of sensor data being received is different than any of the local/fixed sensors, this may suggest that local/fixed/provided sensors of the new data type should be introduced into the environment to accommodate baseline testing of sensors when trust 408 of received data is an issue.

Just like other crowd sourced data systems (like Waze), the system is vulnerable to data poisoning attacks (e.g. the famous Los Angeles residents redirecting traffic out of their neighborhoods by faking traffic congestion). However, the effect of such attacks could be minimized by sending high quality sensors and using the data to call out and potentially dismiss any erroneous data.

Figure 5:
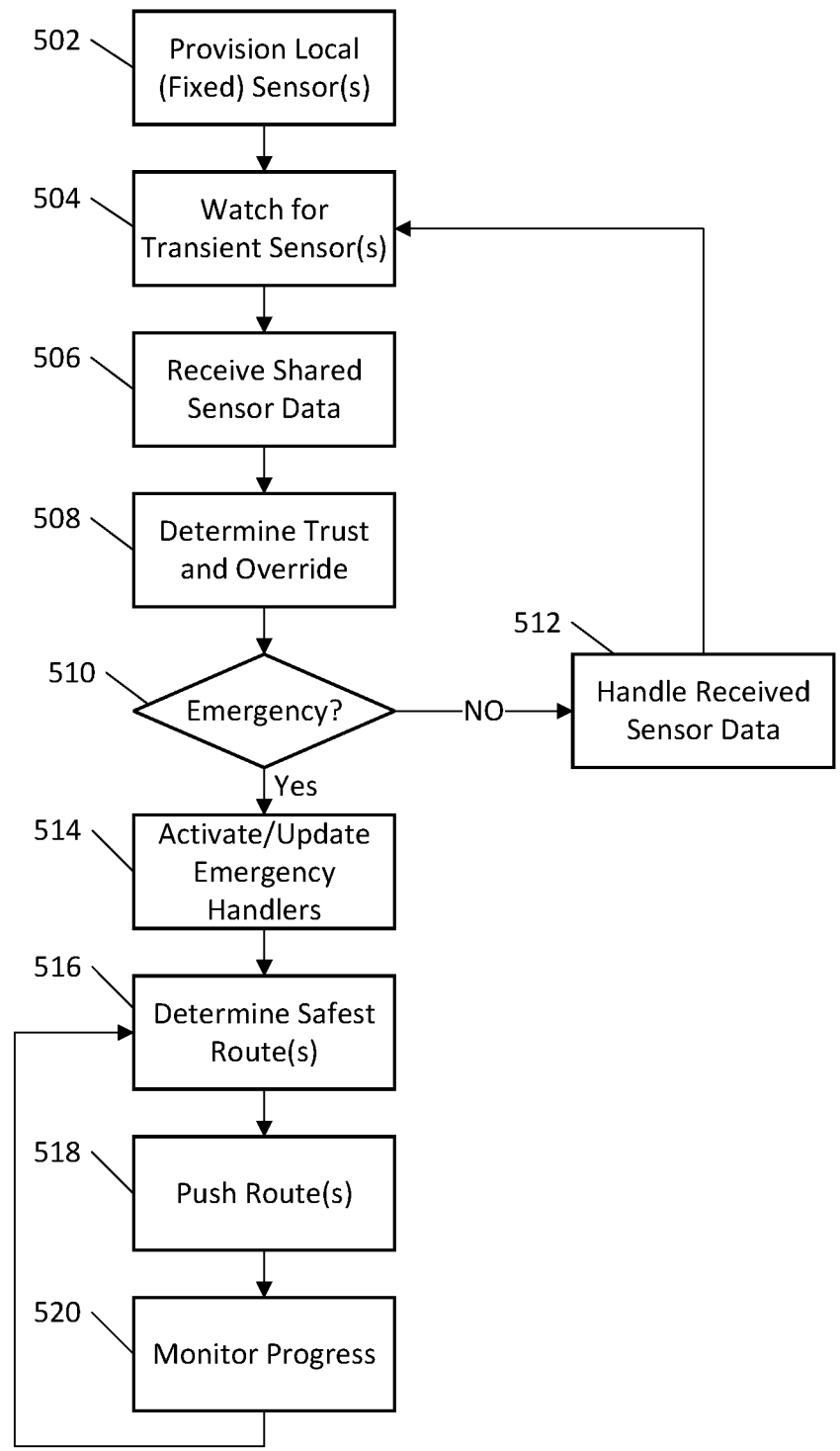
FIG. 5 illustrates an exemplary flowchart 500.

FIG. 5 illustrates an exemplary flowchart 500. This embodiment concerns using aggregated sensor data to assist with emergency response handling. In this embodiment, as with FIG. 4, local (fixed, e.g., non-transitory) sensors may be provisioned 502. In this embodiment, these sensors may be located along evacuation routes for an area. An aggregator may, as discussed above, watch 504 for transient sensor(s) data sharing 506. For expository convenience, it is assumed this illustrated embodiment may determine trust and need for trust override 508, which may include performing FIG. 4 items 408-416 trust determination, data flagging/corroboration, encryption handling, and data override determination, including allowing receiving 506 data in case of emergency or other exigent circumstance.

In this embodiment, let's assume there are workers are in an environment having multiple ingress/egress routes and potentially hazardous conditions, such as miners working a mine, or workers in a factory handling various dangerous chemicals or gasses. Local/fixed sensors may be placed throughout the mine/factory, including along routes of ingress/egress. Local/fixed sensors as well as transient sensors may monitor for safety concerns. If 510 there is a determination there is no emergency, then received sensor data may be handled as discussed previously and processing resume with watching 504 for more transient sensor input. However, if there is an emergency, e.g., a tunnel collapse, air quality concern, chemical spill, etc., then emergency handlers may be activated 514. It will be appreciated a variety of measures may be planned and activating emergency handlers includes putting these measures into place.

In one embodiment, the known ingress/egress routs may be inspected to determine 516 safest routes out of or into an affected area, e.g., the mine/factory. It will be appreciated safe and more particularly, unsafe, routes may be determined in part based on local/fixed sensors along ingress/egress routes. If one route has a sensor sensing hazardous conditions, then that route may be avoided in favor of another. If no route is considered safe, perhaps the best of poor choices may be made. In one embodiment, workers may be carrying devices with safety-related sensors and/or equipment may be regularly traversing the mine/factory, and route safety may be determined based on an inspection of sensor sharing occurring throughout an affected area. In this embodiment, determining 516 the safest route(s) may be based at least in part on a mapping of the area based on safety data shared by transient and local/fixed sensors to identify the best route into or out of the affected area.

Once the safest route is determined 516, it may be pushed 518 to devices in at least the affected area if not the entire factory/mine. It will be appreciated that the safest route for one person in the mine/factory may be different for another. In one embodiment, if 510 there is an emergency, the location of sensors is used to determine 516 a safest route for each sensor (or designated lead sensor in cluster of co-located sensors) and the exit route presented to the sensor or device containing the sensor to assist a person using the sensor to avoid the hazard. It will be appreciated that the pushed 518 safety route may be used in a variety of forms. For example, if workers are wearing vests, they may be outfitted with lights, text displays, digital displays, audio outputs, haptic output, projections, etc. that may be activated by the pushed safety route and used to guide the worker to safety. There may also be fixed lights, displays, projectors, video cameras, and the like that may be coordinated with worker safety/guidance equipment. It will be appreciated feedback loops may be employed to continually monitor 520 exit progress and update the safest route based at least in part on progress toward exiting, and changes in the environment, e.g., if a previously safe route becomes unsafe, this may require re-determining 516 the safest route(s) and pushing 518 updated route(s) information.

The present disclosure is described with reference to flowchart illustrations and/or block diagrams of methods, apparatus (systems) and computer program products according to embodiments of the disclosure. It will be understood each block of the flowchart illustrations and/or block diagrams, and combinations of blocks in the flowchart illustrations and/or block diagrams, may be implemented by computer program instructions. These computer program instructions, as discussed with respect to FIG. 3, may be provided to a processor of a general purpose computer, special purpose computer, or other programmable data processing apparatus to produce a machine, such that the instructions, which execute via the processor of the computer or other programmable data processing apparatus, provide for implementing the functions/acts specified in the flowchart and/or block diagram block or blocks.

Various aspects of the inventive embodiments may be appreciated in part through the following examples.

Example 1 may be a system including an aggregator to aggregate data to be received over at least one data channel from sensors including at least first and second sensors, the sensors including a selected one or more of transitory and fixed sensors, the system comprising: the first one of the sensors to provide first sensed data of a first type to the aggregator; the second one of the sensors to provide second sensed data of a second type to the aggregator; the aggregator to receive selected ones of the first and second sensed data from the sensors, and provide at least one virtual sensor corresponding to the selected ones of the first and second sensed data.

Example 2 may be example 1, wherein the first and second sensors are transitory and a third sensor is fixed.

Example 3 may be example 1, the aggregator further to evaluate the first sensed data for validity, and based on validity, to provide a virtual sensor corresponding to the first sensor.

Example 4 may be example 3, wherein validity is determined based at least in part on comparing the first sensed data to a selected one or more of the second sensed data, or a third sensed data from a third sensor that is equivalent to the first sensed data.

Example 5 may be example 1, wherein a context associated with the first sensor controls sharing of data by the first sensor with the aggregator.

Example 6 may be example 1, further comprising: a first environment having at least temporarily associated therewith the aggregator and the first and second sensors; a second environment having at least temporarily associated therewith a second aggregator and a third sensor to share its sensor data with at least the second aggregator; and a global aggregator to receive data from the first and second aggregator.

Example 7 may be example 6, wherein the first and second environment are geographically separate and communicatively coupled by a network.

Example 8 may be example 1, wherein the aggregator further to evaluate sensed data for an emergency condition, and based on the evaluation, to activate an emergency handler.

Example 9 may be example 8, wherein the emergency handler is to determine a response to the emergency and push the response to selected ones of the sensors.

Example 10 may be a method for an aggregator to receive sensor data from sensors and provide virtual sensors corresponding to selected ones of the sensors, comprising: receiving a first sensor data from a first sensor having a first type; receiving a second sensor data from a second sensor having a second type; instantiating a virtual third sensor to provide data corresponding to at least the first sensor data; and instantiating a virtual fourth sensor to provide sensor data based at least in part on a combination of the first and second sensor data.

Example 11 may be example 10, wherein the virtual fourth sensor data has a third type derived from at least the combination of the first and second sensor data.

Example 12 may be example 11, in which the aggregator has a fixed sensor associated therewith, the method further comprising the virtual fourth sensor generating derivative sensor data based on an analysis of the first and second sensor data in combination with sensor data from the fixed sensor.

Example 13 may be example 10, further comprising: the aggregator receiving data sensed by the second sensor from the first sensor; wherein the first sensor operates as a data transfer proxy for the second sensor.

Example 14 may be example 10, further comprising: detecting arrival of the first sensor; evaluating a first trust value for the first sensor; and accepting the first sensor data of the first sensor based at least in part on the trust value.

Example 15 may be example 14, further comprising: sharing the first sensor data in accord with a first context associated with the first sensor; and encrypting at least a portion of the first data shared with the aggregator.

Example 16 may be example 14, further comprising: detecting arrival of the second sensor; evaluating a second trust value for the second sensor; and accepting sensor data from either the first or second sensor having a higher trust value.

Example 17 may be example 10, further comprising: detecting an emergency associated with at least the first sensor; determining a safety strategy for at least the first sensor; and pushing the safety strategy to at least the first sensor.

Example 18 may be example 17, in which the aggregator has an output associated therewith, the method further comprising: providing at least a portion of the safety strategy to the output; monitoring progress of at least the first sensor in responding to the safety strategy; and updating selected ones of the first sensor and the output with a revised safety strategy based at least in part on the progress of the first sensor.

Example 19 may be one or more non-transitory computer-readable media having instructions, which when executed, provide for a device to receive sensor data from sensors and provide virtual sensors corresponding to selected ones of the sensors, and to provide for: receive a first sensor data from a first sensor having a first type; receive a second sensor data from a second sensor having a second type; instantiate a virtual third sensor to provide data corresponding to at least the first sensor data; and instantiate a virtual fourth sensor to provide sensor data based at least in part on a combination of the first and second sensor data.

Example 20 may be example 19, wherein the device has a fixed sensor associated therewith, and the virtual fourth sensor data has a third type derived from at least the combination of the first and second sensor data, the media further having instructions to direct the virtual fourth sensor to generate derivative sensor data based on an analysis of the first and second sensor data in combination with sensor data from the fixed sensor.

Example 21 may be example 19 having further instructions to direct the device to: detect arrival of the first sensor; evaluate a first trust value for the first sensor; and accept the first sensor data of the first sensor based at least in part on the trust value.

Example 22 may be example 21 having further instructions to direct the device to: share the first sensor data in accord with a first context associated with the first sensor.

Example 23 may be example 21 having further instructions to direct the device to: detect arrival of the second sensor; evaluate a second trust value for the second sensor; and accept sensor data from either the first or second sensor having a higher trust value.

Example 24 may be example 19 having further instructions to direct the device to: detect an emergency associated with at least the first sensor; determine a safety strategy for at least the first sensor; and push the safety strategy to at least the first sensor.

Example 25 may be example 19, in which the device has an output associated therewith, and the media having further instructions to direct the device to: provide at least a portion of the safety strategy to the output; monitor progress of at least the first sensor in responding to the safety strategy; and update selected ones of the first sensor and the output with a revised safety strategy based at least in part on the progress of the first sensor. It will be appreciated the device of examples 19-25 may, for example, be an aggregator, may have an aggregator disposed therein, or may be disposed within an aggregator.

Example 26 may be a system including an aggregator means to aggregate data to be received over at least one data channel from sensor means including at least first and second sensors, the sensors including a selected one or more of transitory and fixed sensors, the system comprising: the first one of the sensor means to provide first sensed data of a first type to the aggregator; the second one of the sensor means to provide second sensed data of a second type to the aggregator; the aggregator means to receive selected ones of the first and second sensed data from the sensor means, and provide at least one virtual sensor corresponding to the selected ones of the first and second sensed data.

Example 27 may be example 26, wherein the first and second sensor means are transitory and a third sensor is fixed.

Example 28 may be example 26, the aggregator means further to evaluate the first sensed data for validity, and based on validity, to provide a virtual sensor corresponding to the first sensor.

Example 29 may be example 3, wherein validity is determined based at least in part on comparing the first sensed data to a selected one or more of the second sensed data, or a third sensed data from a third sensor that is equivalent to the first sensed data.

Example 30 may be example 26, wherein a context associated with the first sensor controls sharing of data by the first sensor with the aggregator means.

Example 31 may be example 26, further comprising: a first environment having at least temporarily associated therewith the aggregator means and the first and second sensor means; a second environment having at least temporarily associated therewith a second aggregator means and a third sensor to share its sensor data with at least the second aggregator means; and a global aggregator means to receive data from the first and second aggregator means.

Example 32 may be example 31, wherein the first and second environment are geographically separate and communicatively coupled by a network.

Example 33 may be example 26, wherein the aggregator means further to evaluate sensed data for an emergency condition, and based on the evaluation, to activate an emergency handler.

Example 34 may be example 33, wherein the emergency handler is to determine a response to the emergency and push the response to selected ones of the sensor means.

Example 35 may be an apparatus for an aggregator to receive sensor data from sensors and provide virtual sensors corresponding to selected ones of the sensors, comprising: means for receiving a first sensor data from a first sensor having a first type; means for receiving a second sensor data from a second sensor having a second type; means for instantiating a virtual third sensor to provide data corresponding to at least the first sensor data; and means for instantiating a virtual fourth sensor to provide sensor data based at least in part on a combination of the first and second sensor data.

Example 36 may be example 10, wherein the virtual fourth sensor data has a third type derived from at least the combination of the first and second sensor data.

Example 37 may be example 36, in which the aggregator has a fixed sensor associated therewith, the method further comprising the virtual fourth sensor generating derivative sensor data based on an analysis of the first and second sensor data in combination with sensor data from the fixed sensor.

Example 38 may be example 35, further comprising: the aggregator receiving data sensed by the second sensor from the first sensor; wherein the first sensor operates as a data transfer proxy for the second sensor.

Example 39 may be example 35, further comprising: means for detecting arrival of the first sensor; means for evaluating a first trust value for the first sensor; and means for accepting the first sensor data of the first sensor based at least in part on the trust value.

Example 40 may be example 39, further comprising: means for sharing the first sensor data in accord with a first context associated with the first sensor; and means for encrypting at least a portion of the first data shared with the aggregator.

Example 41 may be example 39, further comprising: means for detecting arrival of the second sensor; means for evaluating a second trust value for the second sensor; and means for accepting sensor data from either the first or second sensor having a higher trust value.

Example 42 may be example 35, further comprising: detecting an emergency associated with at least the first sensor; determining a safety strategy for at least the first sensor; and pushing the safety strategy to at least the first sensor.

Example 43 may be example 42, in which the aggregator has an output associated therewith, the method further comprising: means for providing at least a portion of the safety strategy to the output; means for monitoring progress of at least the first sensor in responding to the safety strategy; and means for updating selected ones of the first sensor and the output with a revised safety strategy based at least in part on the progress of the first sensor.

Example 44 may be any of examples 19 or 20 having further instructions to provide for: detecting arrival of the first sensor; evaluating a first trust value for the first sensor; and accepting the first sensor data of the first sensor based at least in part on the trust value.

Example 45 may be any of examples 19-21 having further instructions to provide for: sharing the first sensor data in accord with a first context associated with the first sensor.

Example 46 may be any of examples 19-22 having further instructions to provide for: detecting arrival of the second sensor; evaluating a second trust value for the second sensor; and accepting sensor data from either the first or second sensor having a higher trust value.

Example 47 may be any of examples 19-23 having further instructions to provide for: detecting an emergency associated with at least the first sensor; determining a safety strategy for at least the first sensor; and pushing the safety strategy to at least the first sensor.

Example 48 may be any of examples 19-24, in which the aggregator has an output associated therewith, and the media having further instructions to provide for: providing at least a portion of the safety strategy to the output; monitoring progress of at least the first sensor in responding to the safety strategy; and updating selected ones of the first sensor and the output with a revised safety strategy based at least in part on the progress of the first sensor.

Example 49 may be any of examples 1 or 2, the aggregator further to evaluate the first sensed data for validity, and based on validity, to provide a virtual sensor corresponding to the first sensor.

Example 50 may be any of examples 1-4, wherein a context associated with the first sensor controls sharing of data by the first sensor with the aggregator.

Example 51 may be any of examples 1-5, further comprising: a first environment having at least temporarily associated therewith the aggregator and the first and second sensors; a second environment having at least temporarily associated therewith a second aggregator and a third sensor to share its sensor data with at least the second aggregator; and a global aggregator to receive data from the first and second aggregator.

Example 52 may be any of examples 1-7, wherein the aggregator further to evaluate sensed data for an emergency condition, and based on the evaluation, to activate an emergency handler.

Example 53 may be any of examples 10-12, further comprising: the aggregator receiving data sensed by the second sensor from the first sensor; wherein the first sensor operates as a data transfer proxy for the second sensor.

Example 54 may be any of examples 10-13, further comprising: detecting arrival of the first sensor; evaluating a first trust value for the first sensor; and accepting the first sensor data of the first sensor based at least in part on the trust value.

Example 55 may be any of examples 10-16, further comprising: detecting an emergency associated with at least the first sensor; determining a safety strategy for at least the first sensor; and pushing the safety strategy to at least the first sensor.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A system including an aggregator to aggregate data to be received over at least one data channel from sensors including at least first and second sensors, the sensors including a selected one or more of transitory and fixed sensors, and the sensors may have an associated trust value, the system comprising:
   the first one of the sensors to provide first sensed data of a first type to the aggregator;
   the second one of the sensors to provide second sensed data of a second type to the aggregator;
   the aggregator to
     receive selected ones of the first and second sensed data from the sensors,
     provide at least one virtual sensor corresponding to the selected ones of the first and second sensed data, and
     associate a trust value with the virtual sensor, the trust value based at least in part on trust values, if any, associated with either the first or second sensors.

2. The system of claim 1, wherein the first and second sensors are transitory and a third sensor is fixed.

3. The system of claim 1, the aggregator further to evaluate the first sensed data for validity, and based on validity, to provide a virtual sensor corresponding to the first sensor.

4. The system of claim 3, wherein validity is determined based at least in part on comparing the first sensed data to a selected one or more of the second sensed data, or a third sensed data from a third sensor that is equivalent to the first sensed data.

5. The system of claim 1, wherein a context associated with the first sensor controls sharing of data by the first sensor with the aggregator.

6. The system of claim 1, further comprising:
   a first environment having at least temporarily associated therewith the aggregator and the first and second sensors;
   a second environment having at least temporarily associated therewith a second aggregator and a third sensor to share its sensor data with at least the second aggregator; and
   a global aggregator to receive data from the first and second aggregator.

7. The system of claim 6, wherein the first and second environment are geographically separate and communicatively coupled by a network.

8. The system of claim 1, wherein the aggregator is further to evaluate sensed data for an emergency condition, and based on the evaluation, to activate an emergency handler.

9. The system of claim 8, wherein the emergency handler is to determine a response to the emergency and push the response to selected ones of the sensors.

10. A method for a device to receive sensor data from sensors which may have an associated trust value and provide virtual sensors corresponding to selected ones of the sensors, comprising:
receiving a first sensor data from a first sensor having a first type and a trust value;
receiving a second sensor data from a second sensor having a second type; and
instantiating a virtual third sensor to provide selected data corresponding to at least the first sensor data based at least in part on the trust value.

11. The method of claim 10, wherein:
instantiating a virtual fourth sensor to provide sensor data based at least in part on a combination of the first and second sensor data, wherein the virtual fourth sensor data has a third type derived from at least the combination of the first and second sensor data.

12. The method of claim 11, in which an aggregator has a fixed sensor associated therewith, the method further comprising the virtual fourth sensor generating derivative sensor data based on an analysis of the first and second sensor data in combination with sensor data from the fixed sensor.

13. The method of claim 10, further comprising:
the aggregator receiving data sensed by the second sensor from the first sensor;
wherein the first sensor operates as a data transfer proxy for the second sensor.

14. A method for a device to receive sensor data from sensors and provide virtual sensors corresponding to selected ones of the sensors, comprising:
receiving a first sensor data from a first sensor having a first type;
receiving a second sensor data from a second sensor having a second type;
instantiating a virtual third sensor to provide data corresponding to at least the first sensor data; and
instantiating a virtual fourth sensor to provide sensor data based at least in part on a combination of the first and second sensor data;
detecting arrival of the first sensor;
evaluating a first trust value for the first sensor; and
accepting the first sensor data of the first sensor based at least in part on the first trust value.

15. The method of claim 14, further comprising:
sharing the first sensor data in accord with a first context associated with the first sensor; and
at least a portion of the first sensor data shared with an aggregator.

16. The method of claim 14, further comprising:
detecting arrival of the second sensor;
evaluating a second trust value for the second sensor; and
accepting sensor data from either the first or second sensor having a higher trust value.

17. The method of claim 10, further comprising:
detecting an emergency associated with at least the first sensor;
determining a safety strategy for at least the first sensor; and
pushing the safety strategy to at least the first sensor.

18. The method of claim 17, in which the aggregator has an output associated therewith, the method further comprising:
providing at least a portion of the safety strategy to the output;
monitoring progress of at least the first sensor in responding to the safety strategy; and
updating selected ones of the first sensor and the output with a revised safety strategy based at least in part on the progress of the first sensor.

19. One or more non-transitory computer-readable media having instructions, which when executed, provide for a device to receive sensor data from sensors and provide virtual sensors corresponding to selected ones of the sensors, and to provide for:
receive a first sensor data from a first sensor having a first type;
receive a second sensor data from a second sensor having a second type;
instantiate a virtual third sensor to provide data corresponding to at least the first sensor data; and
instantiate a virtual fourth sensor to provide sensor data based at least in part on a combination of the first and second sensor data;
detect arrival of the first sensor;
evaluate a first trust value for the first sensor; and
accept the first sensor data of the first sensor based at least in part on the first trust value.

20. The media of claim 19, wherein the device has a fixed sensor associated therewith, and the virtual fourth sensor data has a third type derived from at least the combination of the first and second sensor data, the media further having instructions to direct the virtual fourth sensor to generate derivative sensor data based on an analysis of the first and second sensor data in combination with sensor data from the fixed sensor.

21. The media of claim 19 having further instructions to direct the device to:
share the first sensor data in accord with a first context associated with the first sensor.

22. The media of claim 19 having further instructions to direct the device to:
detect arrival of the second sensor;
evaluate a second trust value for the second sensor; and
accept sensor data from either the first or second sensor having a higher trust value.

23. The media of claim 19 having further instructions to direct the device to:
detect an emergency associated with at least the first sensor;
determine a safety strategy for at least the first sensor; and
push the safety strategy to at least the first sensor.

24. The media of claim 19, in which the device has an output associated therewith, and the media having further instructions to direct the device to:
provide at least a portion of a safety strategy to the output;
monitor progress of at least the first sensor in responding to the safety strategy; and
update selected ones of the first sensor and the output with a revised safety strategy based at least in part on the progress of the first sensor.

25. The system of claim 1, further comprising the aggregator to:

receive sensed data from a third sensor having an associated high trust value;

compare sensed data from the third sensor with sensed data from a selected sensor having a lower trust value to determine a reliability of the selected sensor; and increase the trust value associated with the selected sensor based at least in part on the reliability.

26. The system of claim 1, further comprising the aggregator to:

receive sensed data from a third sensor;

determine the third sensor has an associated high trust value; and provide the at least one virtual sensor corresponding to sensed data of the third sensor and the selected ones of the first and second sensed data.

27. The media of claim 19 having further instructions to direct the device to:

receive sensed data from a trusted sensor having an associated high trust value;

compare sensed data from the trusted sensor with sensed data from a selected sensor having a lower trust value to determine a reliability of the selected sensor; and increase the trust value associated with the selected sensor based at least in part on the reliability.

28. The media of claim 19 having further instructions to direct the device to:

receive sensed data from a trusted sensor having an associated high trust value; and instantiate at least one of the first or second virtual sensor to provide sensor data based at least in part on sensed data from the trusted sensor.

* * * * *